United States Patent
Fujiwara et al.

(10) Patent No.: US 11,680,055 B2
(45) Date of Patent: Jun. 20, 2023

(54) CRYSTALS

(71) Applicant: NIPPON SHINYAKU CO., LTD., Kyoto (JP)

(72) Inventors: Toshio Fujiwara, Paramus, NJ (US); Joanna Bis, Cary, NC (US); Senthil Kumar Kusalakumari Sukumar, Raleigh, NC (US)

(73) Assignee: NIPPON SHINYAKU CO., LTD., Kyoto (JP)

( * ) Notice: Subject to any disclaimer, the term of this patent is extended or adjusted under 35 U.S.C. 154(b) by 0 days.

(21) Appl. No.: 16/650,106

(22) PCT Filed: Sep. 27, 2018

(86) PCT No.: PCT/JP2018/035830
§ 371 (c)(1),
(2) Date: Mar. 24, 2020

(87) PCT Pub. No.: WO2019/065793
PCT Pub. Date: Apr. 4, 2019

(65) Prior Publication Data
US 2020/0223823 A1  Jul. 16, 2020

(30) Foreign Application Priority Data
Sep. 28, 2017  (JP) ................................ 2017-187297

(51) Int. Cl.
*C07D 401/14* (2006.01)
(52) U.S. Cl.
CPC ........ *C07D 401/14* (2013.01); *C07B 2200/13* (2013.01)
(58) Field of Classification Search
CPC .......................... C07D 401/14; C07B 2200/13
See application file for complete search history.

(56) References Cited

U.S. PATENT DOCUMENTS

| | | | | |
|---|---|---|---|---|
| 8,673,891 B2 * | 3/2014 | Fujihara | ..................... | A61P 9/10 514/210.02 |
| 2011/0288065 A1 * | 11/2011 | Fujihara | ..................... | A61P 9/14 514/210.02 |
| 2013/0131082 A1 | 5/2013 | Fujihara et al. | | |

FOREIGN PATENT DOCUMENTS

| | | |
|---|---|---|
| CN | 102307869 A | 1/2012 |
| KR | 10-2011-0120932 | 11/2011 |
| MX | 2011008243 A | 8/2011 |
| RU | 2535217 C2 | 12/2014 |
| WO | WO 2010/090290 A1 | 8/2010 |
| WO | WO 2012/005299 A1 | 1/2012 |
| WO | WO 2012/020786 A1 | 2/2012 |
| WO | WO 2012/020787 A1 | 2/2012 |

OTHER PUBLICATIONS

Asahara, *Solvents handbook*, Kodansha Ltd., pp. 47-51 (1985).
Ashizawa, "Optimization of salt and crystalline forms, and crystallization technique", *Pharm. Tech. Japan*, 18(10): 81-96 (2002).
Campbell et al., "The Myeloproliferative Disorders.", *New England Journal of Medicine*, 355(23): 2452-2466 (2006).
Catlett-Falcone et al., "Constitutive Activation of Stat3 Signaling Confers Resistance to Apoptosis in Human U266 Myeloma Cells", *Immunity*, 10(1): 105-115 (1999).
Ceesay et al., "The JAK2 V617F mutation is rare in RARS but common in RARS-T", *Leukemia*, 20: 2060-2062 (2006).
Chemistry handbook: Applied chemistry part—6$^{th}$ edition, Chapter 4: Chemosynthesis technique, *The Chemical Society of Japan*, pp. 178, (Jan. 30, 2003).
Gaikwad et al., "Prevalence and clinical correlates of JAK2 mutations in Down syndrome acute lymphoblastic leukaemia", *British Journal of Haematology*, 144(6): 930-932 (2008).
Hart et al., "Pharmacodynamic (PD) Biomarker Assay Validation for SB1518, a Novel Oral JAK2 Inhibitor in Phase 1 Clinical Trials for Advanced Leukemias, Myeloproliferative Diseases and Lymphoma.", 51$^{st}$ ASH Annual Meeting and Exposition, *Blood*, 114(22): 1888 (2009).
Heinrich et al., "Principles of interleukin (IL)-6-type cytokine signalling and its regulation", *Biochemical Journal*, 374(1): 1-20 (2003).
Hirayama, Organic Compound Crystal Preparation Handbook—Principle and Knowhow, *Maruzen Inc.*, 57-84 (Jul. 25, 2008).
Kralovics et al., "A Gain-of-Function Mutation of JAK2 in Myeloproliferative Disorders", *New England Journal of Medicine*, 352(17): 1779-1790 (2005).
Meier et al., "Recurrent numerical aberrations of JAK2 and deregulation of the JAK2-STAT cascade in lymphomas", *Modern Pathology*, 22(3): 476-487 (2009).
Melzner et al., "Biallelic mutation of SOCS-1 impairs JAK2 degradation and sustains phospho-JAK2 action in the MedB-1 mediastinal lymphoma line", *Blood*, 105(6): 2535-2542 (2005).
Mottok et al., "Inactivating SOCS1 mutations are caused by aberrant somatic hypermutation and restricted to a subset of B-cell lymphoma entities", *Blood*, 114(20): 4503-4506 (2009).

(Continued)

*Primary Examiner* — Paul V Ward
(74) *Attorney, Agent, or Firm* — Leydig, Voit & Mayer, Ltd.

(57) ABSTRACT

A main object of the present invention is to provide new crystals of (S)-$N^2$-[1-(4-fluorophenyl)ethyl]-4-(1-methyl-1H-pyrazol-4-yl)-$N^6$-(pyrazin-2-yl)pyridine-2,6-diamine maleate (hereinafter, referred to as "compound A"). A Form-I crystal of the compound A, showing diffraction peaks in its X-ray powder diffraction spectrum at least at the following angles of diffraction 2θ: 6.9 degrees, 9.4 degrees, 12.5 degrees, 15.1 degrees, 16.4 degrees, 18.3 degrees, 19.0 degrees, 24.9 degrees, 25.4 degrees, 27.3 degrees, and 27.7 degrees, wherein X-ray powder diffraction spectrum is obtained by using Cu Kα radiation (λ=1.54 Å). A Form-II crystal of the compound A, showing diffraction peaks in its X-ray powder diffraction spectrum at least at the following angles of diffraction 2θ: 6.9 degrees, 9.2 degrees, 12.4 degrees, 14.8 degrees, 16.5 degrees, 18.1 degrees, 18.5 degrees, 19.8 degrees, 23.6 degrees, 24.9 degrees, and 27.7 degrees, wherein X-ray powder diffraction spectrum is obtained by using Cu Kα radiation (λ=1.54 Å).

6 Claims, 6 Drawing Sheets

(56) References Cited

OTHER PUBLICATIONS

Mottok et al., "Somatic hypermutation of SOCS1 in lymphocyte-predominant Hodgkin lymphoma is accompanied by high JAK2 expression and activation of STAT6", *Blood*, 110(9): 3387-3390 (2007).
Mullighan et al., "JAK mutations in high-risk childhood acute lymphoblastic leukemia", *Proceedings of the National Academy of Science U.S.A.*, 106(23): 9414-9418 (2009).
Narazaki et al., "Activation of JAK2 kinase mediated by the interleukin 6 signal transducer gp130", *Proceedings of the National Academy of Science U.S.A.*, 91(6): 2285-2289 (1994).
Neilson et al., "Coactivation of Janus Tyrosine Kinase (Jak)1 Positively Modulates Prolactin-Jak2 Signaling in Breast Cancer: Recruitment of ERK and Signal Transducer and Activator of Transcription (Stat)3 and Enhancement of Akt and Stat5a/b Pathways", *Molecular Endocrinology*, 21(9):2218-2232 (2007).
Ogura et al., "Interleukin-17 Promotes Autoimmunity by Triggering a Positive-Feedback Loop via Interleukin-6 Induction", *Immunity*, 29(4): 628-636 (2008).
Oikawa et al., "Detection of a new JAK2 D620E mutation in addition to V617F in a patient with polycythemia vera", *Leukemia*, 20(12):2210-2211 (2006).
Pardanani et al., "MPL515 mutations in myeloproliferative and other myeloid disorders: a study of 1182 patients", *Blood*, 108(10): 3472-3476 (2006).
Pikman et al., "MPLW515L Is a Novel Somatic Activating Mutation in Myelofibrosis with Myeloid Metaplasia", *PLoS Medicine*, 3(7): 1140-1151 (2006).
Samanta et al., "Janus Kinase 2: A Critical Target in Chronic Myelogenous Leukemia", *Cancer Research*, 66(13): 6468-6472 (2006).
Shioji, Solid formulation manufacturing technique, popular edition, *Tokyo: CMC Publishing Co., Ltd.*, pp. 9, 12, 13 (Jan. 27, 2003).
Sprague et al., "Inflammatory cytokines in vascular dysfunction and vascular disease", *Biochemical Pharmacology*, 78(6): 539-552 (2009).
Steiner et al., "Interleukin-6 Overexpression Induces Pulmonary Hypertension", *Circulation Research*, 104(2): 236-244 (2009).
Tefferi et al., "IDH1 and IDH2 mutation studies in 1473 patients with chronic-, fibrotic- or blast-phase essential thrombocythemia, polycythemia vera or myelofibrosis", *Leukemia*, 24(7): 1302-1309 (2010).
Tefferi et al., "TET2 mutations and their clinical correlates in polycythemia vera, essential thrombocythemia and myelofibrosis", *Leukemia*, 23(5): 905-911 (2009).
Valentino et al., "JAK/STAT signal transduction: Regulators and implication in hematological malignancies", *Biochemical Pharmacology*, 71(6): 713-721 (2006).
Younes et al., "Phase-I Study of the Novel Oral JAK-2 Inhibitor SB1518 in Patients with Relapsed Lymphoma: Evidence of Clinical and Biologic Activity.", 51$^{st}$ ASH Annual Meeting and Exposition, *Blood*, 114(22): 588 (2009).
Yu et al., "STATs in cancer inflammation and immunity: a leading role for STAT3", *Nature Reviews Cancer*, 9(11):798-809 (2009).
Japan Patent Office, International Search Report in International Application No. PCT/JP2018/035830 (dated Dec. 18, 2018).
Japan Patent Office, Written Opinion in International Application No. PCT/JP2018/035830 (dated Dec. 18, 2018).
International Bureau of WIPO, International Preliminary Report on Patentability in International Application No. PCT/JP2018/035830 (dated Mar. 31, 2020).
Caira, M., "Crystalline polymorphism of organic compounds." Topics in Current Chemistry, vol. 198: 163-208 (1998).
Morissette et al., "High-throughput crystallization: polymorphs, salts, co-crystals and solvates of pharmaceutical solids." *Advanced Drug Delivery Reviews*, 56(3): 275-300 (2004).
Federal Institute of Industrial Property, Office Action issued in Russian Patent Application No. 2020114659/04 (dated Apr. 8, 2022).
China National Intellectual Property Administration, Office Action issued in Chinese Application No. 201880062018.0 (dated May 30, 2022).
Matsumoto, Mitsuo, *Pharmaceutics Manual*, 1st Edition, pp. 28, 76, and 80 (1989).
Peterson et al., "Expanding the Scope of Crystal Form Evaluation in Pharmaceutical Science", *J Pharm Pharmaceut Sci*, vol. 9(3): pp. 317-326 (2006).
Noriyu, Takata, "Drug Substance Form Screening and Selection in the Drug Discovery Phase", *Pharm Stage*, vol. 6(10): pp. 20-25 (2007).
Japan Patent Office, Decision of Refusal issued in Japanese Patent Application No. 2019-545595 (dated Feb. 27, 2023).
Mexican Industral Property Office, Office Action issued in Mexican Patent Application No. MX/a/2020/007177 (dated Mar. 16, 2023).
Choi et al., "Technique to Control Polymorphs of Active Pharmaceutical Ingredient", *News & Information for Chemical Engineers*, vol. 28(1): pp. 38-46 (2010).
Korean Intellectual Property Office, Office Action issued in Korean Patent Application No. 10-2020-7010737 (dated Apr. 12, 2023).

\* cited by examiner

CRYSTALS

CROSS-REFERENCE TO RELATED APPLICATIONS

This patent application is the U.S. national phase of International Application No. PCT/JP2018/035830, filed on Sep. 27, 2018, which claims the benefit of Japanese Patent Application No. 2017-187297, filed Sep. 28, 2017, the disclosures of which are incorporated herein by reference in their entireties for all purposes.

TECHNICAL FIELD

The present invention relates to new crystals of (S)-$N^2$-[1-(4-fluorophenyl)ethyl]-4-(1-methyl-1H-pyrazol-4-yl)-$N^6$-(pyrazin-2-yl)pyridine-2,6-diamine maleate (hereinafter, referred to as "compound A").

[Chem. 1]

BACKGROUND ART

Pharmaceutical products are required to have qualities that are maintained for a long period of time under various conditions during distribution, storage, and the like. Therefore, compounds that serve as active ingredients are required to have high physicochemical stability. Thus, as an active ingredient for a pharmaceutical product, a crystal that is expected to have high stability is employed in general.

In the course of screening a crystal of an active ingredient for a pharmaceutical product, it is difficult to find an optimum condition for obtaining a crystal. In addition, even when a crystal has been obtained, the presence of crystalline polymorphisms often poses a problem. This problem arises because physicochemical stability differs depending on the crystal form.

In addition, if an inappropriate crystal form is selected to be employed as an active ingredient for a pharmaceutical product, decrease in purity, crystal form transformation, and the like could occur depending on an external environment during storage. This makes it difficult to maintain the compound at a constant quality. Thus, depending on the crystal form, an unexpected situation such as a decreased drug efficacy, side effects, and the like could occur. Therefore, when a crystal of a compound to serve as an active ingredient for a pharmaceutical product has been successfully obtained, strict evaluations and studies regarding the physicochemical stability as to the crystalline polymorphism thereof need to be performed.

However, the presence or absence of a crystalline polymorphism or a stable crystal form cannot be predicted from the structure of a compound. Further, there are also cases where a compound that cannot form a crystal exists. Thus, various conditions that allow formation of a crystal need to be studied for each compound.

Meanwhile, since the compound A has an excellent JAK2 tyrosine kinase inhibitory action, the compound A is expected to exhibit therapeutic effects on various diseases (for example, see PATENT DOCUMENT 1, PATENT DOCUMENT 2). However, at present, it is not known whether or not a crystalline polymorphism is present, nor is it known whether or not a crystal can be formed in the first place. Thus, it has been an important issue to obtain an optimum crystal in developing a pharmaceutical product.

CITATION LIST

Patent Document

[PATENT DOCUMENT 1] WO2010/090290A1
[PATENT DOCUMENT 2] WO2012/020787A1

Non Patent Document

[NON-PATENT DOCUMENT 1] L. Richeldi, et al., 2006, Leukemia, 20, 2210-2211
[NON-PATENT DOCUMENT 2] Peter J. Campbell, et al., 2006, New England Journal of Medicine, 355, 2452-2466
[NON-PATENT DOCUMENT 3] A Tefferi, et al., 2009, Leukemia, 23, 905-911
[NON-PATENT DOCUMENT 4] A Tefferi, et al., 2010, Leukemia, 24, 1302-1309
[NON-PATENT DOCUMENT 5] Robert Kralovics, et al., 2005, New England Journal of Medicine, 352, 1779-1790
[NON-PATENT DOCUMENT 6] Yana Pikman, et al., 2006, PLoS Medicine, 3, 1140-1151
[NON-PATENT DOCUMENT 7] Animesh D, et al., 2006, Blood, 108, 3472-3476
[NON-PATENT DOCUMENT 8] Lyne Valentino, et al., 2006, Biochemical Pharmacology, 71, 713-721
[NON-PATENT DOCUMENT 9] MM Ceesay, et al., 2006, Leukemia, 20, 2260-2261
[NON-PATENT DOCUMENT 10] C. Mullighan, et al., 2009, Proceedings of the National Academy of Science U.S.A, 106, 9414-9418
[NON-PATENT DOCUMENT 11] A. Gaikwad, et al., 2008, British Journal of Haematology, 144, 930-932
[NON-PATENT DOCUMENT 12] Ajoy K. Samanta, et al., 2006, Cancer Research, 66, 6468-6472
[NON-PATENT DOCUMENT 13] Cecile Meier, et al., 2009, Modern Pathology, 22, 476-487
[NON-PATENT DOCUMENT 14] Anja Mottok, et al., 2007, Blood, 110, 3387-3390
[NON-PATENT DOCUMENT 15] Anja Mottok, et al., 2009, Blood, 114, 4503-4506
[NON-PATENT DOCUMENT 16] Ingo Melzner, et al., 2005, Blood, 105, 2535-2542
[NON-PATENT DOCUMENT 17] Anas Young, et al., 2009, 51st ASH ANNUAL MEETING AND EXPOSITION
[NON-PATENT DOCUMENT 18] Stefan Hert, et al., 2009, 51st ASH ANNUAL MEETING AND EXPOSITION
[NON-PATENT DOCUMENT 19] L. Neilson, et al., 2007, Molecular Endocrinology, 21, 2218-2232
[NON-PATENT DOCUMENT 20] H. Yu, et al., 2009, Nature Reviews Cancer, 9, 798-809
[NON-PATENT DOCUMENT 21] H. Ogura, et al., 2008, Immunity, 29, 628-636
[NON-PATENT DOCUMENT 22] R. Catlett-Falcone, et al., 1999, Immunity, 10, 105-115

[NON-PATENT DOCUMENT 23] M. Narazaki, et al., 1994, Proceedings of the National Academy of Science U.S.A, 91, 2285-2289

[NON-PATENT DOCUMENT 24] P. Heinrich, et al., 2003, Biochemical Journal, 374, 1-20

[NON-PATENT DOCUMENT 25] M. Steiner, et al., 2009, Circulation Research, 104, 236-244

[NON-PATENT DOCUMENT 26] H. Alexander, et al., 2009, Biochemical Pharmacology, 78, 539-552

SUMMARY OF INVENTION

Problems to be Solved by the Invention

An object of the present invention is to provide a crystal, of the compound A, that has excellent in physicochemical stability, and to provide a pharmaceutical composition that contains the crystal as an active ingredient.

Means for Solving the Problems

The present inventors conducted thorough research in order to solve the above problem. As a result, the present inventors succeeded in forming a crystal of the compound A, found that Form-I and Form-II crystalline polymorphisms exist, and completed the present invention.

The present invention can include, for example, the following (1) to (5) below.

(1) A Form-I crystal of the compound A (hereinafter, referred to as "Form-I crystal of the present invention"), showing diffraction peaks in its X-ray powder diffraction spectrum at least at the following angles of diffraction 2θ: 6.9 degrees, 9.4 degrees, 12.5 degrees, 15.1 degrees, 16.4 degrees, 18.3 degrees, 19.0 degrees, 24.9 degrees, 25.4 degrees, 27.3 degrees, and 27.7 degrees, wherein X-ray powder diffraction spectrum is obtained by using Cu Kα radiation (λ=1.54 Å), (2) a Form-I crystal of the present invention, having an endothermic peak at 203±3° C. in differential scanning calorimetry, (3) a Form-II crystal of the compound A (hereinafter, referred to as "Form-II crystal of the present invention"), showing diffraction peaks in its X-ray powder diffraction spectrum at least at the following angles of diffraction 2θ: 6.9 degrees, 9.2 degrees, 12.4 degrees, 14.8 degrees, 16.5 degrees, 18.1 degrees, 18.5 degrees, 19.8 degrees, 23.6 degrees, 24.9 degrees, and 27.7 degrees, wherein X-ray powder diffraction spectrum is obtained by using Cu Kα radiation (λ=1.54 Å), (4) a Form-II crystal of the present invention, having an endothermic peak at 200±3° C. in differential scanning calorimetry, and (5) a pharmaceutical composition containing the crystal according to any one of (1) to (4) as an active ingredient (hereinafter, referred to as "pharmaceutical composition of the present invention").

When specifying a diffraction angle 2θ of a diffraction peak in Examples and the claims of the present invention, an obtained value should be understood to be in a range of the value±0.2 degrees, and preferably in a range of the value±0.1 degrees.

When specifying an absorption peak of an infrared absorption spectrum (hereinafter, referred to as "IR spectrum") in Examples and the claims of the present invention, an obtained value should be understood to be in a range of the value±2 cm$^{-1}$, and preferably in a range of the value±1 cm$^{-1}$.

When specifying an endothermic peak of a differential scanning calorimeter (hereinafter, referred to as "DSC") in Examples and the claims of the present invention, an obtained value should be understood to be in a range of the value±3° C., and preferably in a range of the value±2° C.

EMBODIMENTS FOR CARRYING OUT THE INVENTION

A. Form-I Crystal of the Present Invention

A Form-I crystal of the present invention is characterized by showing diffraction peaks in its X-ray powder diffraction spectrum at least at the following angles of diffraction 2θ: 6.9 degrees, 9.4 degrees, 12.5 degrees, 15.1 degrees, 16.4 degrees, 18.3 degrees, 19.0 degrees, 24.9 degrees, 25.4 degrees, 27.3 degrees, and 27.7 degrees, wherein X-ray powder diffraction spectrum is obtained by using Cu Kα radiation (λ=1.54 Å). Preferably, the Form-I crystal of the present invention is characterized by showing diffraction peaks at 19.6 degrees, 21.8 degrees, and 23.5 degrees, in addition to the above diffraction peaks.

The Form-I crystal of the present invention is characterized by showing, in an infrared absorption spectrum (KBr method), absorption peaks at wavenumbers of 1617 cm$^{-1}$, 1509 cm$^{-1}$, 1351 cm$^{-1}$, 1224 cm$^{-1}$, and 866 cm$^{-1}$.

The Form-II crystal of the present invention is characterized by having an endothermic peak at 203° C. in differential scanning calorimetry.

The Form-I crystal of the present invention can be obtained by, for example, a method according to Example 1 described later.

B. Form-II Crystal of the Present Invention

A Form-II crystal of the present invention is characterized by showing diffraction peaks in its X-ray powder diffraction spectrum at least at the following angles of diffraction 2θ: 6.9 degrees, 9.2 degrees, 12.4 degrees, 14.8 degrees, 16.5 degrees, 18.1 degrees, 18.5 degrees, 19.8 degrees, 23.6 degrees, 24.9 degrees, and 27.7 degrees, wherein X-ray powder diffraction spectrum is obtained by using Cu Kα radiation (λ=1.54 Å). Preferably, the Form-II crystal of the present invention is characterized by showing diffraction peaks at 20.5 degrees, 21.2 degrees, and 21.9 degrees, in addition to the above diffraction peaks.

The Form-II crystal of the present invention is characterized by showing, in an infrared absorption spectrum (KBr method), absorption peaks at wavenumbers of 1617 $cm^{-1}$, 1507 $cm^{-1}$, 1350 $cm^{-1}$, 1224 $cm^{-1}$, and 865 $cm^{-1}$.

The Form-II crystal of the present invention is characterized by having an endothermic peak at 200° C. in differential scanning calorimetry.

The Form-II crystal of the present invention can be obtained by, for example, a method according to Example 2 described later.

C. Pharmaceutical Use—Pharmaceutical Composition of the Present Invention

The compound A according to the present invention has an excellent JAK2 tyrosine kinase inhibitory action (see PATENT DOCUMENT 1, for example).

Therefore, the Form-I crystal of the present invention and the Form-II crystal of the present invention (hereinafter, collectively referred to as the "crystal of the present invention") or the pharmaceutical composition of the present invention can be used as a prophylactic agent or therapeutic agent for, for example, cancers [e.g., blood cancers {e.g., polycythemia vera (see NON-PATENT DOCUMENT 1, for example), essential thrombocythemia, idiopathic myelofibrosis (see NON-PATENT DOCUMENT 2, for example), myeloproliferative neoplasm (chronic myeloproliferative disorder) (see NON-PATENT DOCUMENTS 5, 6, 7, 8, for example) such as secondary myelofibrosis (see NON-PATENT DOCUMENTS 3, 4, for example), osteomyelodysplasia syndrome (see NON-PATENT DOCUMENT 9, for example), acute lymphocytic leukemia (see NON-PATENT DOCUMENTS 10, 11, for example), acute myeloid leukemia (see NON-PATENT DOCUMENT 8, for example), secondary acute myeloid leukemia (see NON-PATENT DOCUMENTS 3, 4, for example), chronic myeloid leukemia (see NON-PATENT DOCUMENT 12, for example), and multiple myeloma} (see NON-PATENT DOCUMENT 8, for example), malignant lymphoma (see NON-PATENT DOCUMENTS 13-18, for example), and solid cancers {e.g., prostate cancer, breast cancer (see NON-PATENT DOCUMENT 19, for example)}], and diseases of which pathological conditions involve IL-6 transduced through JAK2 tyrosine kinase {e.g., inflammatory diseases (e.g., rheumatoid arthritis, inflammatory bowel disease, osteoporosis, multiple sclerosis), and angiopathy (e.g., pulmonary hypertension, arteriosclerosis, aneurysm, varicose vein)}(see NON-PATENT DOCUMENTS 20-26, for example).

"Malignant lymphoma" is not limited in particular, as long as the lymphoma involves JAK2 tyrosine kinase. Examples of malignant lymphoma include Hodgkin lymphoma and non-Hodgkin lymphoma, including recurrent intractable ones.

Examples of "Non-Hodgkin lymphoma" include B-cell lymphoma and NK/T-cell lymphoma.

Examples of "Hodgkin lymphoma" include nodular lymphocyte predominant Hodgkin lymphoma and classical Hodgkin lymphoma.

Examples of "B-cell lymphoma" include precursor B-cell lymphoblastic leukemia/lymphoma, follicular lymphoma, mantle-cell lymphoma, small lymphocytic lymphoma/chronic lymphocytic leukemia, marginal zone B-cell lymphoma, extranodal marginal zone lymphoma, splenic marginal zone lymphoma, nodal marginal zone lymphoma, lymphoplasmacytic lymphoma, diffuse large B-cell lymphoma, mediastinal large-B cell lymphoma, and Burkitt's lymphoma.

Examples of "NK/T-cell lymphoma" include precursor T-cell lymphoblastic leukemia/lymphoma, T-cell prolymphocytic leukemia, T-cell large granular lymphocytic leukemia, aggressive NK-cell leukemia, adult T-cell leukemia/lymphoma, mycosis fungoides, Sezary syndrome, primary cutaneous CD30 positive T-cell lymphoproliferative disorders, extranodal NK/T-cell lymphoma, nasal type, enteropathy-associated T-cell lymphoma, hepatosplenic T-cell lymphoma, subcutaneous panniculitis-like T-cell lymphoma, angioimmunoblastic T-cell lymphoma, peripheral T-cell lymphoma, unspecified, and anaplastic large-cell lymphoma.

Examples of "secondary myelofibrosis" include secondary myelofibrosis subsequently developed from polycythemia vera, and secondary myelofibrosis subsequently developed from essential thrombocythemia.

Examples of "secondary acute myeloid leukemia" include secondary acute myeloid leukemia subsequently developed from polycythemia vera, secondary acute myeloid leukemia subsequently developed from essential thrombocythemia, and secondary acute myeloid leukemia subsequently developed from myelofibrosis.

When administered as a medicament, the crystal of the present invention is administered as is, or in a form of being contained in a pharmaceutically acceptable nontoxic and inactive carrier, for example, in a range of 0.1% to 99.5%, preferably in a range of 0.5% to 90%.

Examples of the carrier include solid, semi-solid, or liquid diluents, fillers, and other auxiliaries for formulations. One type or two types or more of these can be used.

The pharmaceutical composition of the present invention can be in any form of preparation for oral administration such as bulk powder, capsule, tablet, sugar-coated tablet, granule, powder, suspension, liquid, syrup, elixir, and troche, and parenteral preparations such as injection and suppository. The pharmaceutical composition of the present invention may be a sustained release preparation. Among these, an oral administration preparation such as tablet is particularly preferred.

The powder can be produced by making the crystal of the present invention into an appropriate fine size.

The powder preparation can be produced in such a manner that the crystal of the present invention is made into an appropriate fine size, and then is mixed with a pharmaceutical carrier that has been similarly made into a fine size, such as an edible carbohydrate like starch or mannitol. A flavoring agent, a preservative, a dispersant, a colorant, a perfume, and the like may be added thereto as desired.

The capsules can be produced in such a manner that a capsule shell such as a gelatin capsule is filled with powder or powder preparation which has been made into a powdery form as described above or into a granulated form as will be described in the section for the tablet. In addition, the capsule can also be produced in such a manner that a lubricant or plasticizer, such as colloidal silica, talc, magnesium stearate, calcium stearate, or solid polyethylene glycol is mixed with powder or powder preparation in a powdery form, and then the mixture is subjected to the filling operation. If a disintegrator or a solubilizer, such as carboxymethylcellulose, carboxymethylcellulose calcium, low substituted hydroxypropylcellulose, croscarmellose sodium, carboxymethyl starch sodium, calcium carbonate, or sodium carbonate, is added, the efficacy of the medicament can be improved when the capsule is ingested.

It is also possible to produce a soft capsule by suspending and dispersing fine powder of the crystal of the present invention, in a vegetable oil, polyethylene glycol, glycerin, and a surfactant, and wrapping the resultant with a gelatin sheet.

The tablets can be produced in such a manner that a powder mixture is made by adding an excipient to the crystal of the present invention having been powdered, then is made into granules or slugs, then, a disintegrator or a lubricant is added thereto, and then, the resultant is subjected to tableting.

The powder mixture can be produced by mixing the crystal of the present invention in an appropriately powdered form, with a diluent or a base material. If necessary, a binder (e.g., carboxymethylcellulose sodium, methylcellulose, hydroxypropylmethylcellulose, gelatin, polyvinylpyrrolidone, polyvinyl alcohol), a dissolution retardant (e.g., paraffin), a reabsorption agent (e.g., quaternary salt), an adsorbent (e.g., bentonite, kaolin), and the like may be added.

The granules can be produced in such a manner that the powder mixture is made wet with a binder, for example, a syrup, a starch paste, a gum arabic, a cellulose solution, or a polymer solution, and then stirred and mixed, and then the mixture is dried and ground. Instead of performing granulation of powder as described above, it is also possible that the powder is applied to a tableting machine first, and then, the resultant slug in an incomplete form is ground to produce granules.

When stearic acid, a stearate, talc, mineral oil, or the like is added as a lubricant to the thus-produced granules, the granules can be prevented from sticking to each other.

The tablets can also be produced by, without performing the granulation or slug formation step as described above, mixing the crystal of the present invention with a fluidic inactive carrier, and then directly tableting the mixture.

The thus-produced tablets can be subjected to film coating or sugar coating. A transparent or semitransparent protective coat made of a shellac seal coat, a coat made of sugar or polymer material, or a polish coat made of wax can also be used.

Each of the other oral administration preparations, for example, liquid, syrup, troche, and elixir, can also be prepared in a unit dosage form such that a certain amount thereof contains a certain amount of the crystal of the present invention.

The syrup can be produced by dissolving the crystal of the present invention in an appropriate flavoring aqueous solution. The elixir can be produced by using a nontoxic alcoholic carrier.

The suspension can be produced by dispersing the crystal of the present invention in a nontoxic carrier. If necessary, a solubilizer or an emulsifier (e.g., ethoxylated isostearyl alcohols, polyoxyethylene sorbitol esters), a preservative, a flavor imparting agent (e.g., peppermint oil, saccharin), and the like may be added.

When necessary, a unit dosage formulation for oral administration can be microencapsulated. The formulation can also have extended action time and a sustained release property if the formulation is coated or embedded in polymer, wax, or the like.

The parenteral administration preparation can take a form of a liquid unit dosage form, for example, a solution or a suspension form, such as for subcutaneous, intramuscular, or intravenous injection. The parenteral administration preparation can be produced by suspending or dissolving a certain amount of the crystal of the present invention into a nontoxic liquid carrier that is suited for the purpose of the injection, such as an aqueous or oleaginous medium, and then by sterilizing the suspension or solution. A stabilizer, a preservative, an emulsifier, and the like may also be added.

The suppository can be produced by dissolving or suspending the crystal of the present invention in a low-melting water-soluble or -insoluble solid, such as polyethylene glycol, cacao butter, semisynthetic fats and oils [e.g., WITEPSOL (registered trade mark)], or higher esters (for example, myristyl palmitate), or a mixture thereof.

The dose depends on the state of the patient such as body weight and age, the route of administration, the characteristics and severity of the disease, and the like. However, in general, the amount of the crystal of the present invention for an adult per day is suitably in a range of 0.001 mg to 100 mg, and preferably in a range of 0.01 mg to 10 mg.

Depending on the case, a dose not greater than the above-mentioned amount may be sufficient, or a dose greater than the above-mentioned amount may be necessary. One to several administrations may be given per day, or an administration may be given at an interval of one to several days.

D. Production of Compound A

The compound A can be produced according to the method described in PATENT DOCUMENT 1, for example, but can also be produced according to the production process below.

[Chem. 2]

Step 1 Production of
2,6-dichloro-4-(1-methyl-1H-pyrazol-4-yl)pyridine 2,6-dichloro-4-(1-methyl-1H-pyrazol-4-yl)pyridine can be produced by reacting 2,6-dichloro-4-(4,4,5,5-tetramethyl-1,3,2-dioxaborolan-2-yl)pyridine with 4-iodo-1-methyl-1H-pyrazole in the presence of a palladium catalyst and a base. This reaction can be carried out according to a known method, as a coupling reaction using a palladium catalyst. Examples of a reaction solvent to be used include a mixed solvent of water and an organic solvent (e.g., aromatic hydrocarbons such as toluene and xylene, ethers such as 1,4-dioxane, tetrahydrofuran, 2-methyltetrahydrofuran, and tetrahydropyran, or a mixed solvent thereof). Examples of a palladium catalyst to be used include [1,1'-bis(diphenylphosphino)ferrocene]palladium dichloride dichloromethane complex (hereinafter, referred to as "PdCl$_2$(pddf)-CH$_2$Cl$_2$"), tetrakis(triphenylphosphine)palladium (hereinafter, referred to as "Pd(PPh$_3$)$_4$"), and the like. Examples of the base to be used include potassium carbonate, sodium carbonate, potassium phosphate, sodium phosphate, and the like. For example, the amount of 4-iodo-1-methyl-1H-pyrazole to be used is suitably in a range of 1 to 3 times the molar amount of 2,6-dichloro-4-(4,4,5,5)tetramethyl-1,3,2-dioxaborolan-2-yl)pyridine, and preferably in a range of 1 to 2 times the molar amount thereof. For example, the amount of the palladium catalyst to be used is suitably in a range of 0.02 to 1 times the molar amount of 2,6-dichloro-4-(4,4,5,5)tetramethyl-1,3,2-dioxaborolan-2-yl)pyridine, and preferably in a range of 0.02 to 0.03 times the molar amount thereof. For example, the amount of the base to be used is suitably in a range of 2 to 10 times the molar amount of 2,6-dichloro-4-(4,4,5,5)tetramethyl-1,3,2-dioxaborolan-2-yl)pyridine, and preferably in a range of 3 to 4 times the molar amount thereof. The reaction temperature depends on the kinds of the raw material and reagent to be used, but is usually in a range of 80° C. to 100° C. The reaction time depends on the kinds of the raw material, reagent, and solvent to be used and the reaction temperature, but a suitable reaction time is usually in a range of 1 to 5 hours.

Step 2 Production of Compound A

The compound A can be produced in such a manner that: in the presence of a palladium catalyst, a ligand, and a base, 2,6-dichloro-4-(1-methyl-1H-pyrazol-4-yl)pyridine is reacted with (S)-1-(4-fluorophenyl)ethylamine, and further with 2-aminopyrimidine; and the resultant compound is converted to a maleate salt.

The reaction between 2,6-dichloro-4-(1-methyl-1H-pyrazol-4-yl)pyridine, (S)-1-(4-fluorophenyl) ethylamine, and 2-aminopyrimidine can be carried out by a known method, as a coupling reaction using a palladium catalyst, a ligand, and a base.

Examples of a reaction solvent to be used include aromatic hydrocarbons such as toluene, xylene, and the like, ethers such as tetrahydrofuran, 1,4-dioxane, 2-methyltetrahydrofuran, tetrahydropyran, and the like, and a mixed solvent thereof. Examples of the palladium catalyst to be used include palladium(II) acetate (hereinafter, referred to as "Pd(OAc)$_2$"), tris(dibenzylideneacetone)dipalladium (Pd$_2$(dba)$_3$), bis(acetylacetonato)palladium (Pd(acac)$_2$), PdCl$_2$(pddf)-CH$_2$Cl$_2$, Pd(PPh$_3$)$_4$, and the like. Examples of the ligand to be used include (1)-2,2'-bis(diphenylphosphino)-1,1'-binaphthyl (hereinafter, referred to as "BINAP"), 2-dicyclohexylphosphino-2',4',6'-triisopropylbiphenyl (X-Phos), 2-dicyclohexylphosphino-2',6'-dimethoxybiphenyl (S-Phos), and the like. Examples of the base to be used include potassium t-butoxide, potassium methoxide, potassium ethoxide, sodium t-butoxide, and mixed bases thereof. For example, the amount of (S)-1-(4-fluorophenyl)ethylamine to be used is suitably in a range of 1 to 3 times the molar amount of 2,6-dichloro-4-(1-methyl-1H-pyrazol-4-yl)pyridine, and preferably in a range of 1 to 2 times the molar amount thereof. For example, the amount of the palladium catalyst to be used is suitably in a range of 0.02 to 1 times the molar amount of 2,6-dichloro-4-(1-methyl-1H-pyrazol-4-yl)pyridine, and preferably in a range of 0.02 to 0.03 times the molar amount thereof. For example, the amount of the ligand to be used is suitably in a range of 0.02 to 1 times of the molar amount of 2,6-dichloro-4-(1-methyl-1H-pyrazol-4-yl)pyridine, and preferably in a range of 0.02 to 0.03 times the molar amount thereof. For example, the amount of the base to be used is suitably 1 to 3 times of the molar amount of 2,6-dichloro-4-(1-methyl-1H-pyrazol-4-yl)pyridine, and preferably in range of 1 to 1.5 times of the molar amount thereof. The temperature for reacting (S)-1-(4-fluorophenyl)ethylamine depends on the kinds of the raw material and reagent to be used, but a suitable temperature is usually in a range of 55 to 65° C. The reaction time depends on the kinds of the raw material, reagent, and solvent to be used and the reaction temperature, but a suitable reaction time is usually in a range of 1 to 5 hours.

For example, the amount of 2-aminopyrimidine to be used is suitably in a range of 1 to 3 times the molar amount of 2,6-dichloro-4-(1-methyl-1H-pyrazol-4-yl)pyridine, and preferably in a range of 1 to 2 times the molar amount thereof. When 2-aminopyridine is added to the reaction solution, a base may be further added thereto. For example, the amount of the base to be used is suitably 1 to 3 times the molar amount of 2,6-dichloro-4-(1-methyl-1H-pyrazol-4-yl)pyridine, and preferably in a range of 1 to 1.5 times the molar amount thereof. The temperature for reacting 2-aminopyridine depends on the kinds of the raw material and reagent to be used, but a suitable temperature is usually in a range of 80 to 110° C. The reaction time depends on the kinds of the raw material, reagent, and solvent to be used and the reaction temperature, but a suitable reaction time is usually in a range of 1 to 24 hours.

For example, the amount of maleic acid to be used is suitably in a range of 1 to 5 times of the molar amount of 2,6-dichloro-4-(1-methyl-1H-pyrazol-4-yl)pyridine, and preferably in a range of 1 to 3 times the molar amount thereof. A suitable reaction temperature is usually in a range of 50° C. to 60° C. The reaction time depends on the reaction temperature, but a suitable reaction time is usually in a range of 1 to 24 hours.

Each compound to be used as a raw material, in the production process of the compound A described above, may be a known compound or may be produced according to a known method.

EXAMPLES

The present invention is described in further detail with reference to Examples and Test Examples. However, the present invention is not limited thereto in any way.

The X-ray powder diffraction spectrum was measured by using SmartLab (manufactured by Rigaku Corporation) (optical system: focal method, voltage: 45 kV, current: 200 mA, wavelength: Cu Kα, Soller slit: 5.0°, scanning range: 4 to 40°, scanning rate: 47.3°/minute, sample rotation: 60°/minute).

The IR spectrum was measured by using IR Affinity-1 (manufactured by Shimadzu Corporation) (measurement mode: % Transmittance, accumulation: 32 times, resolution: 2.0, wavenumber range: 400 to 4000 cm$^{-1}$).

The DSC was measured by using of DSC-50 (manufactured by Shimadzu Corporation) (cell: alumina (open), gas: nitrogen (20.0 mL/minute), heating rate: 10.0° C./minute, hold temperature: 300° C., hold time: 0 minutes).

Example 1 Production of Compound A (S)-1-(4-fluorophenyl)ethylamine (23.9 kg), Pd(OAc)$_2$ (1.75 kg), and (±)-BINAP (6.3 kg) were added to a suspension of 2,6-dichloro-4-(1-methyl-1H-pyrazol-4-yl)pyridine (35.6 kg) in tetrahydrofuran (213 L) and toluene (106 L), and the mixture was stirred at 60° C. for 1 hour. Further, potassium t-butoxide (21.0 kg) was added thereto, and the resultant mixture was stirred at 60° C. for 1 hour. The mixture was cooled to room temperature, and 2-aminopyrimidine (17.8 kg) and potassium t-butoxide (19.3 kg) were added thereto, and the resultant mixture was stirred at 90° C. for 5 hours. After the mixture was cooled to 60° C., the organic layer was washed with an ethylenediamine aqueous solution, and then the solvent was distilled off under reduced pressure. Ethyl acetate (356 L) was added to the concentrated residue, and a maleic acid solution (obtained by dissolving maleic acid (21.7 kg) in 2-propanol (71 L)) was added thereto at 55° C., and the resultant mixture was stirred at 55° C. for 30 minutes. The mixture was cooled to 10° C. or lower, and was stirred for 1 hour. The generated precipitate was filtered and washed with ethyl acetate (107 L). The precipitate was dried at 50° C. under reduced pressure to obtain the target compound (35.9 kg).

Example 2 Production of Form-I Crystal of the Present Invention

The compound A (35.9 kg) produced in Example 1, Si-Thiol (manufactured by Biotage Japan Ltd.) (1.76 kg), and activated carbon (1.84 kg) were dissolved at 60° C. in N,N-dimethylformamide (107 L), and the mixture was stirred at 60° C. for 30 minutes. This solution was filtered and washed with N,N-dimethylformamide (72 L), and the obtained filtrate was concentrated under reduced pressure. Ethyl acetate (539 L) was added at 50° C. to the concentrate, and the mixture was gradually cooled, and stirred at 10° C. or lower for 1 hour. Precipitated crystals were collected through filtration and washed with ethyl acetate (108 L). The resultant crystals were dried at 80° C. under reduced pressure, to obtain the Form-I crystal of the present invention (31.6 kg).

Figure 1:
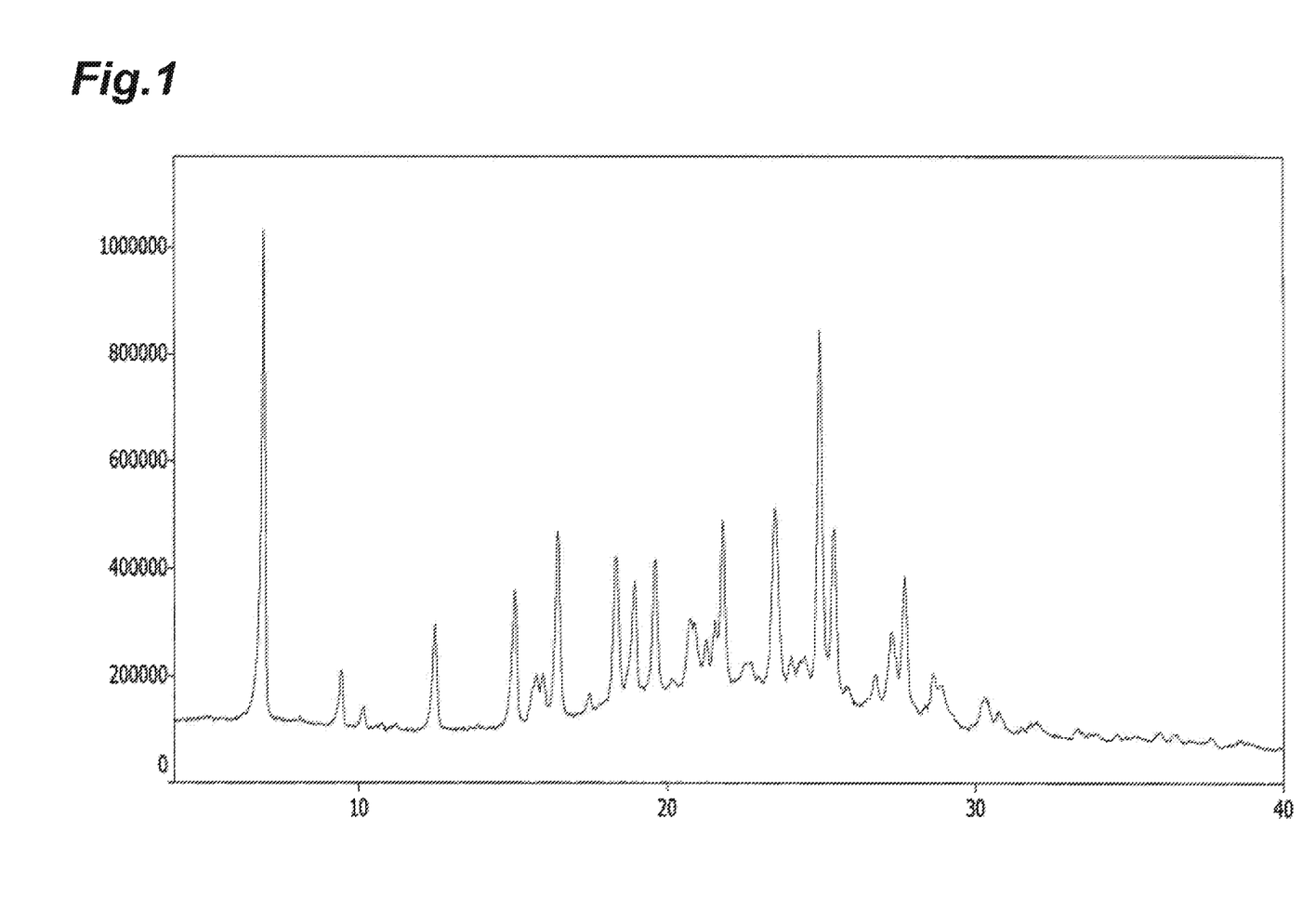
FIG. 1 shows a chart of an X-ray powder diffraction spectrum of a Form-I crystal of the present invention. The vertical axis represents peak intensity (cps), and the horizontal axis represents diffraction angle (2θ[°]).
Figure 3:
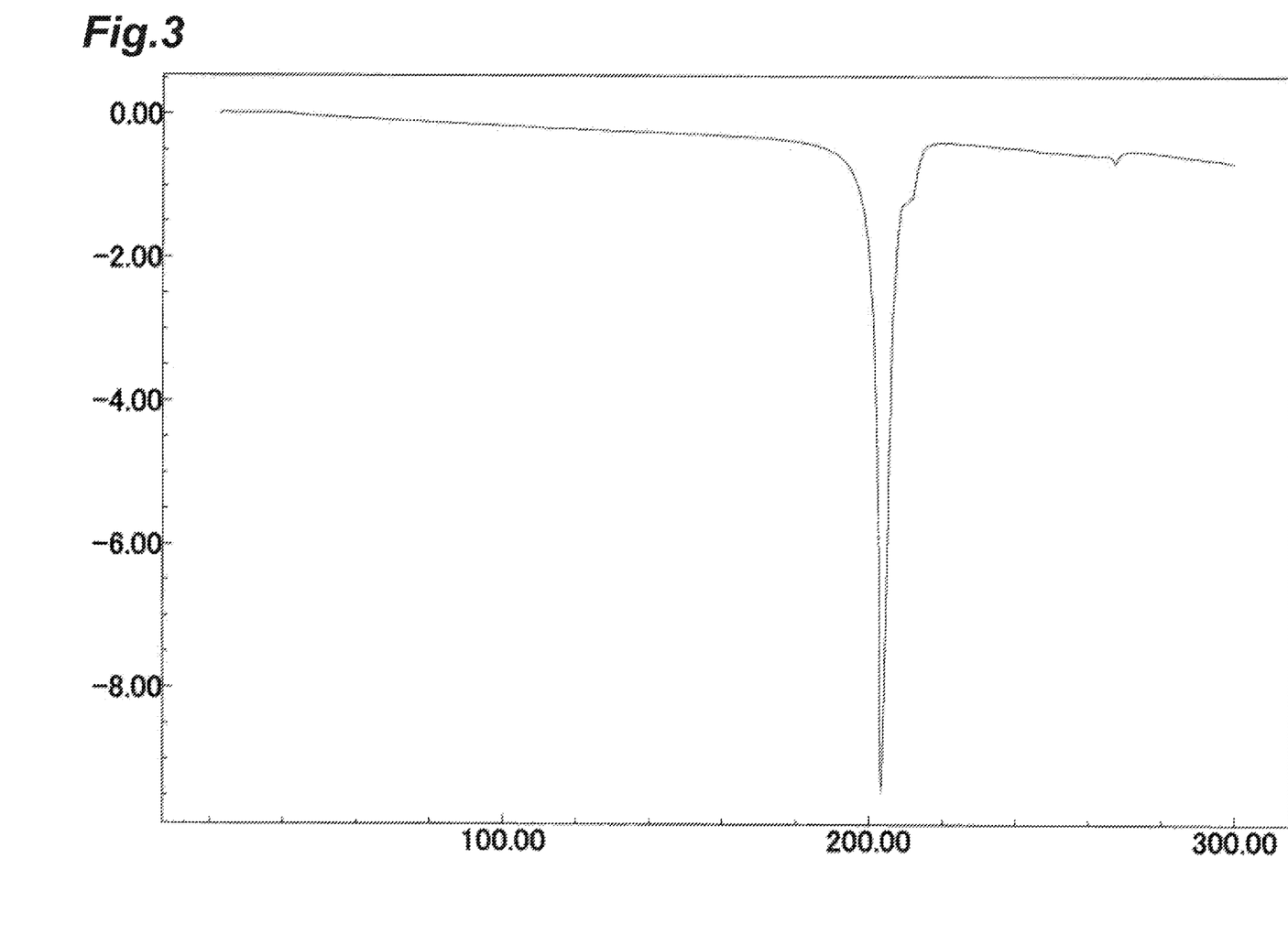
FIG. 3 shows a chart of DSC measurement obtained when the temperature of the Form-I crystal of the present invention was increased by 10° C. per minute. The vertical axis represents exothermic amount (mW) per second (when the value is negative, the value represents an endothermic amount), and the horizontal axis represents temperature (° C.).
Figure 5:
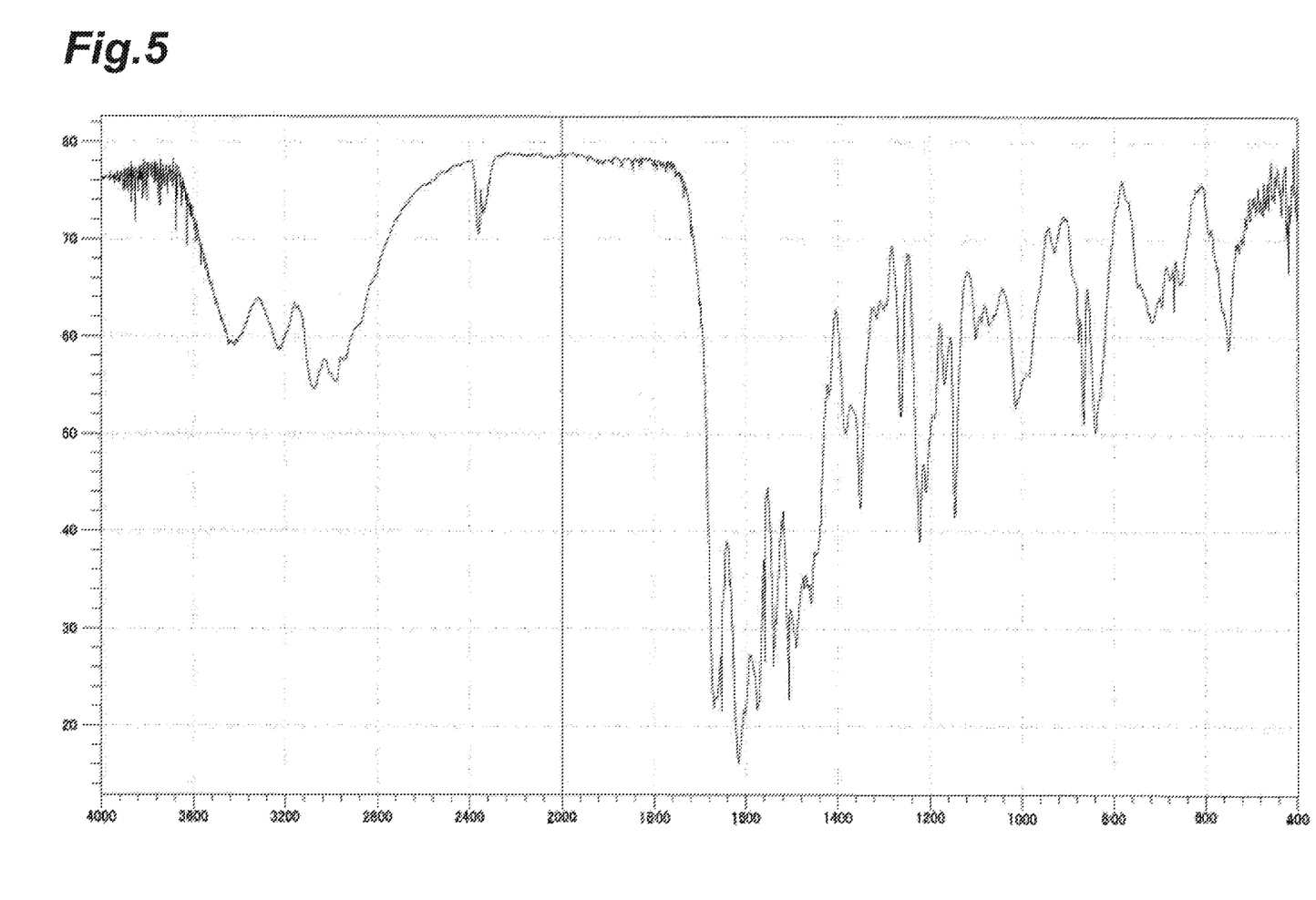
FIG. 5 shows a chart of an IR spectrum of the Form-I crystal of the present invention. The vertical axis represents transmittance (%), and the horizontal axis represents wavenumber (cm$^{-1}$).

The results of measurement of X-ray powder diffraction, DSC measurement, and IR measurement with respect to the Form-I crystal of the present invention are shown in FIG. 1, FIG. 3, and FIG. 5, respectively.

Diffraction angle 2θ: 6.9 degrees, 9.4 degrees, 12.5 degrees, 15.1 degrees, 16.4 degrees, 18.3 degrees, 19.0 degrees, 19.6 degrees, 21.8 degrees, 23.5 degrees, 24.9 degrees, 25.4 degrees, 27.3 degrees, and 27.7 degrees IR absorption peak: 1617 cm$^{-1}$, 1509 cm$^{-1}$, 1351 cm$^{-1}$, 1224 cm$^{-1}$, and 866 cm$^{-1}$ DSC endothermic peak: 203° C.

Example 3 Production of Form-II Crystal of the Present Invention

The compound A (0.5 g) produced in Example 1 was suspended in an 80% acetone aqueous solution (4 mL), and the mixture was stirred at room temperature for 1 hour. The suspension was filtered and washed with a small amount of 80% acetone aqueous solution, water (40 mL) was added to the filtrate, and the mixture was stirred at room temperature for 1 day. Further, the mixture was filtered and washed with a small amount of water, and the filtrate was concentrated under reduced pressure to distill off acetone. After the concentration, the concentrate was stirred at room temperature for 1 hour, and precipitated crystals were collected through filtration and washed with water. The resultant crystals were dried at 60° C. under reduced pressure, to obtain the Form-II crystal of the present invention (0.13 g).

Figure 2:
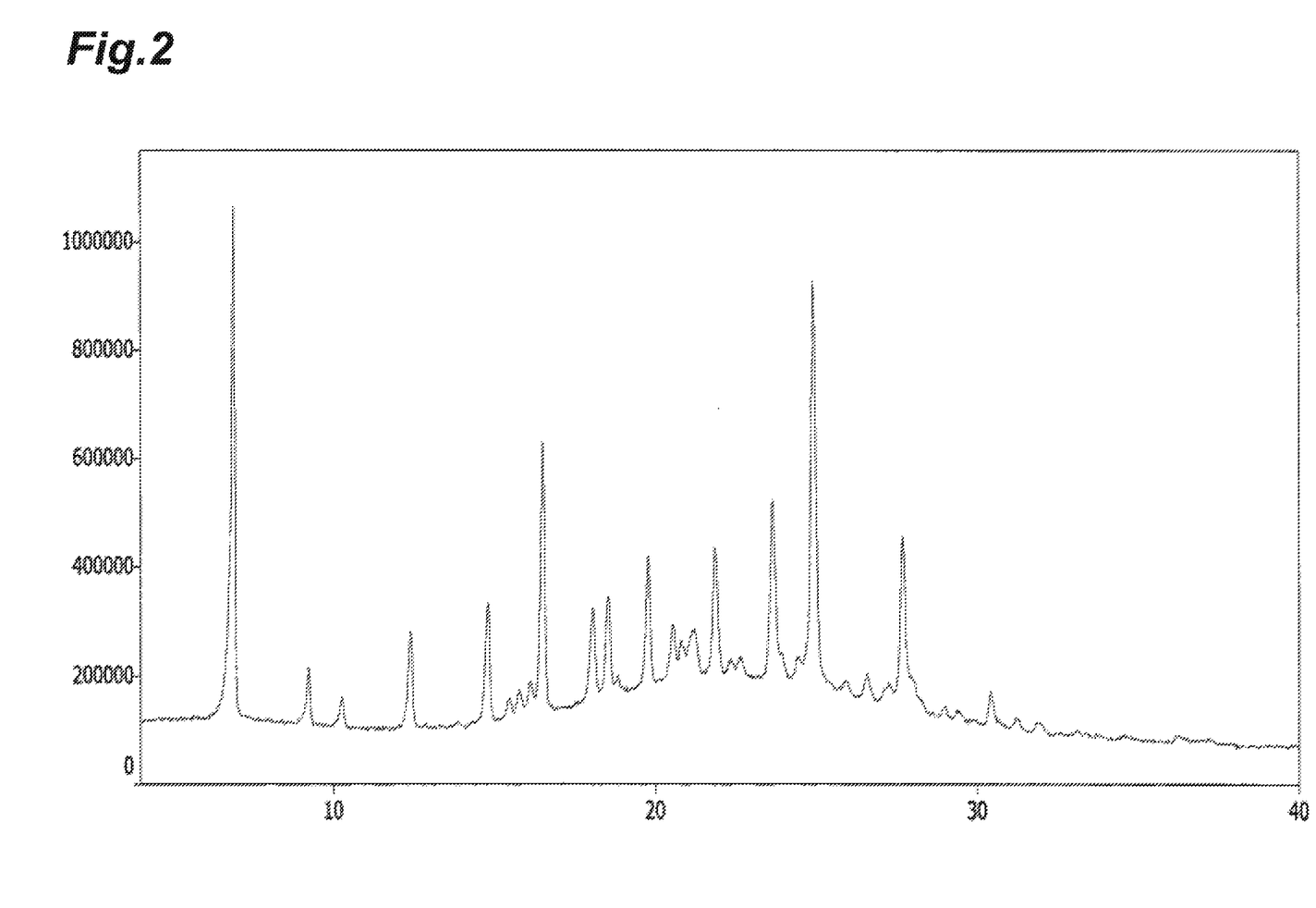
FIG. 2 shows a chart of an X-ray powder diffraction spectrum of a Form-II crystal of the present invention. The vertical axis represents peak intensity (cps), and the horizontal axis represents diffraction angle (2θ[°]).
Figure 4:
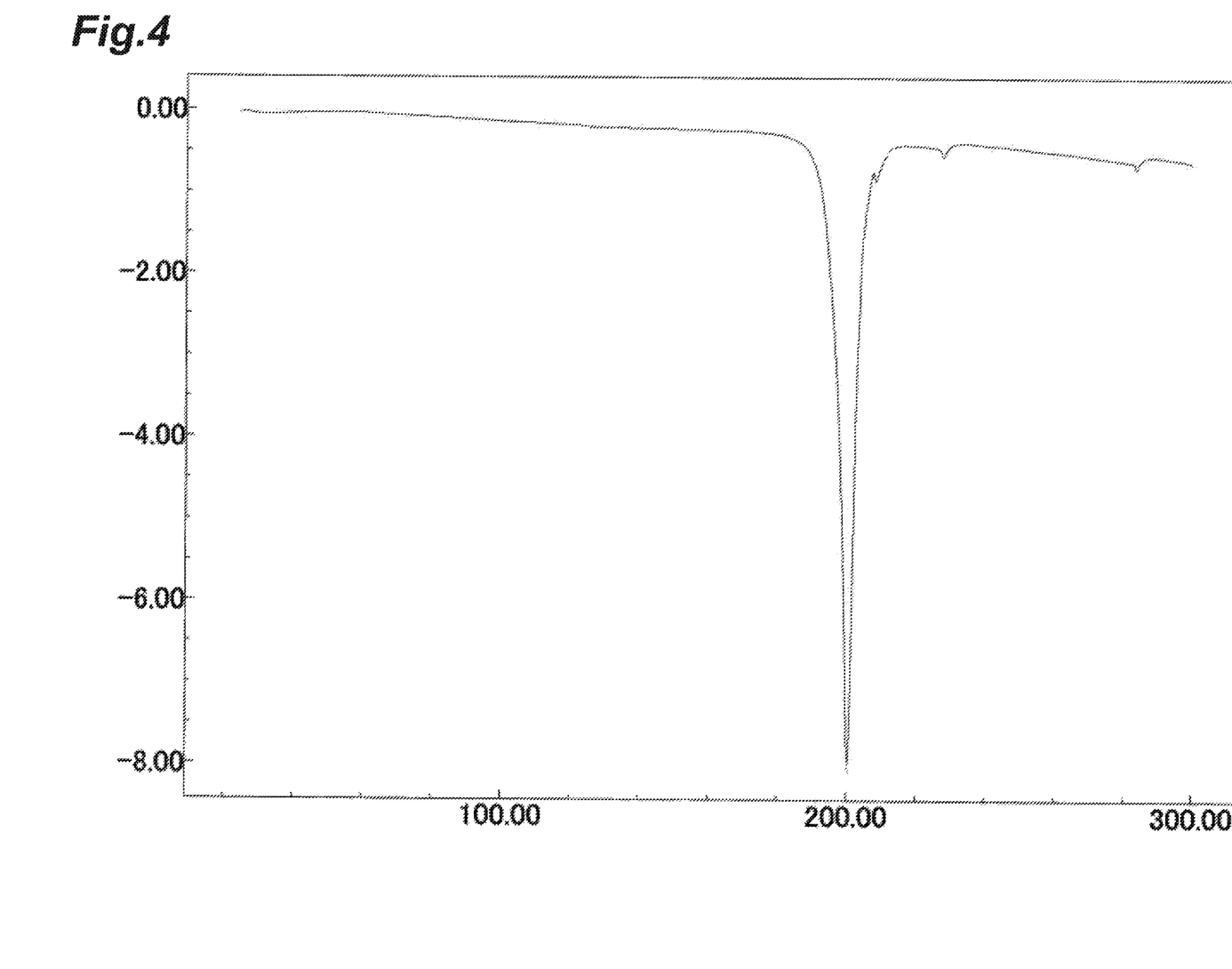
FIG. 4 shows a chart of DSC measurement obtained when the temperature of the Form-II crystal of the present invention was increased by 10° C. per minute. The vertical axis of the chart represents exothermic amount (mW) (when the value is negative, the value represents an endothermic amount), and the horizontal axis represents temperature (° C.).
Figure 6:
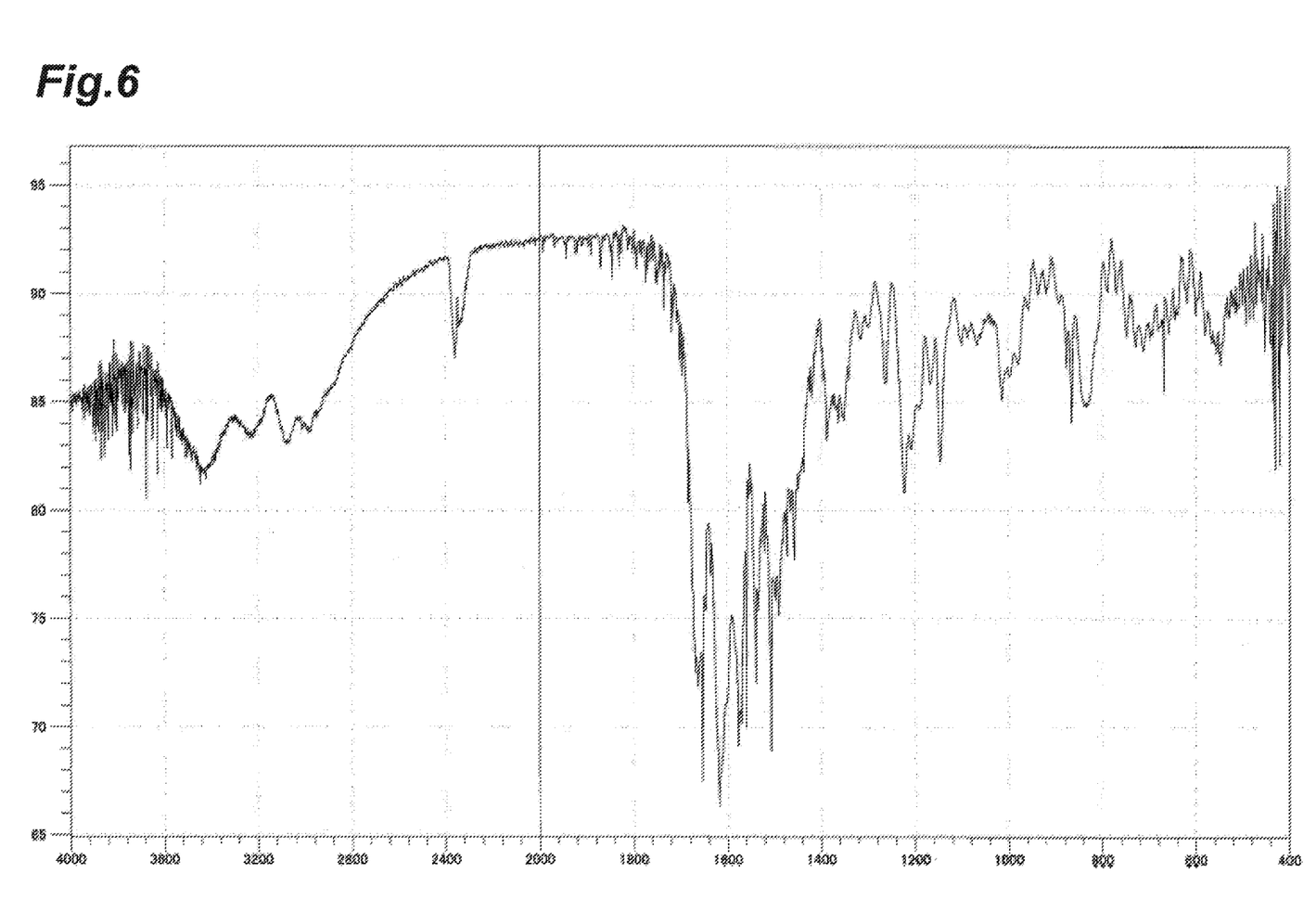
FIG. 6 shows a chart of an IR spectrum of the Form-II crystal of the present invention. The vertical axis represents transmittance (%), and the horizontal axis represents wavenumber (cm$^{-1}$).

The results of measurement of X-ray powder diffraction, DSC measurement, and IR measurement with respect to the Form-II crystal of the present invention are shown in FIG. 2, FIG. 4, and FIG. 6, respectively.

Diffraction angle 2θ: 6.9 degrees, 9.2 degrees, 12.4 degrees, 14.8 degrees, 16.5 degrees, 18.1 degrees, 18.5 degrees, 19.8 degrees, 20.5 degrees, 21.2 degrees, 21.9 degrees, 23.6 degrees, 24.9 degrees, and 27.7 degrees IR absorption peak: 1617 cm$^{-1}$, 1507 cm$^{-1}$, 1350 cm$^{-1}$, 1224 cm$^{-1}$, and 865 cm$^{-1}$ DSC endothermic peak: 200° C.

Test Example 1 Results of Crystallization Experiments Using Various Solvents

Each of various solvents was added to the Form-I crystal of the present invention (several mg), crystals of the compound A were precipitated according to the following operation procedures, and the crystal form of the precipitated crystals was confirmed. The results of the operation procedures 1 to 3 are shown in Table 1 and Table 2, and the results of the operation procedure 4 are shown in Table 3. The symbol "-" in Table 1 to Table 3 means that no precipitate was obtained.

Operation Procedure 1:

Each of various solvents (50 μL) was added to the Form-I crystal of the present invention to make a suspension thereof, and the suspension was stirred for 2 days while repeatedly being cooled and warmed between 4 to 40° C.

Operation Procedure 2:

Each of various solvents (50 μL) was added to the Form-I crystal of the present invention to dissolve the Form-I crystal of the present invention at 40° C. When the Form-I crystal of the present invention did not dissolve, the insolubles was filtered to obtain a solution. The solution was cooled to 4° C. and stirred for 3 days.

Operation Procedure 3:

Each of various solvents (50 μL) was added to the Form-I crystal of the present invention to dissolve the Form-I crystal of the present invention at 40° C. When the Form-I crystal of the present invention did not dissolve, the insolubles was filtered to obtain a solution. The solvent was gradually distilled off at room temperature.

Operation Procedure 4:

Each of various dissolving solvents (minimum volume) was added to the Form-I crystal of the present invention to prepare a saturated solution. Various poor solvents were added thereto.

TABLE 1

| Solvent | Operation procedure 1 | Operation procedure 2 | Operation procedure 3 |
|---|---|---|---|
| water | Form-I | — | — |
| methanol | Form-I | Form-I | Form-I |
| 2-methoxyethanol | Form-I | — | Form-I |
| 1-propanol | Form-I | Form-I | Form-I |

TABLE 1-continued

| Solvent | Operation procedure 1 | Operation procedure 2 | Operation procedure 3 |
|---|---|---|---|
| nitromethane | Form-I | — | — |
| acetonitrile | Form-I | — | — |
| dimethyl sulfoxide | — | — | Form-I |
| acetone | Form-I | Form-I | — |
| methyl ethyl ketone | Form-I | — | Form-I |
| dichloromethane | Form-I | — | Form-I |
| methyl acetate | Form-I | — | — |
| methyl isobutyl ketone | Form-I | — | — |
| chloroform | Form-I | — | — |
| ethyl acetate | Form-I | — | — |
| chlorobenzene | Form-I | — | — |
| tetrahydrofuran | Form-I | — | Form-I |
| 1,4-dioxane | Form-I | solvate | — |
| isopropyl ether | Form-I | — | — |
| toluene | Form-I | — | — |
| cyclohexane | Form-I | — | — |
| heptane | Form-I | — | — |
| 1-butanol | Form-I | — | — |
| 2-propanol | Form-I | — | — |
| trifluoroethanol | — | — | solvate |
| dimethyl carbonate | Form-I | — | — |
| t-butyl methyl ether | Form-I | — | — |
| isopropyl acetate | Form-I | — | — |
| ethanol | Form-I | Form-I | Form-I |
| 1-methoxy-2-propanol | Form-I | — | — |
| cyclohexanone | Form-I | — | Form-I |
| N,N-dimethylformamide | — | — | Form-I |
| 2-methoxyethyl ether | Form-I | — | — |

TABLE 2

| Solvent | Operation procedure 1 | Operation procedure 2 | Operation procedure 3 |
|---|---|---|---|
| methanol:water 95:5 | Form-I | — | Form-I |
| acetonitrile:water 95:5 | Form-I | — | Form-I |
| acetone:water 95:5 | Form-I | — | amorphous |
| tetrahydrofuran:water 95:5 | Form-I | — | Form-I |
| 2-propanol:water 95:5 | Form-I | — | Form-I |
| methanol:water 80:20 | Form-I | Form-I | Form-I |
| 2-propanol:water 80:20 | Form-I | — | Form-I |
| acetonitrile:water 80:20 | Form-I | — | amorphous |
| acetone:water 80:20 | Form-I | — | Form-I |
| 1,4-dioxane:water 80:20 | Form-I | — | Form-I |
| ethanol:water 20:80 | Form-I | — | Form-II |
| acetone:water 20:80 | Form-I | — | Form-I |
| tetrahydrofuran:water 20:80 | Form-I | — | Form-II |
| ethanol:dimethyl sulfoxide 80:20 | Form-I | Form-I | Form-I |
| acetonitrile:dimethyl sulfoxide 80:20 | Form-I | — | Form-I |
| N-methylpyrrolidone | — | — | Form-I |

TABLE 3

| Dissolving solvent | Poor solvent | Crystal form |
|---|---|---|
| dimethyl sulfoxide | diisopropyl ether | — |
| | t-butyl methyl ether | Form-I |
| | ethyl acetate | Form-I |
| | water | — |
| | 2-propanol | Form-I |
| N,N-dimethylformamide | water | Form-I |
| | t-butyl methyl ether | Form-I |
| | diethyl ether | Form-I |
| | isopropyl acetate | Form-I |
| | 2-propanol | Form-I |
| N-methylpyrrolidone | water | Form-I |
| | ethyl acetate | Form-I |
| | toluene | Form-I |
| | 2-propanol | Form-I |
| trifluoroethanol | water | — |
| | diisopropyl ether | Form-I |
| | cyclohexane | — |
| 2-methoxyethanol | water | — |
| | isopropyl acetate | Form-I |
| | cyclohexane | Form-I |
| | t-butyl methyl ether | Form-I |
| acetone:water 80:20 | water | Form-II |
| | 2-propanol | — |
| tetrahydrofuran:water 80:20 | water | Form-I |

As shown above, in the crystallization from various solvents, the Form-I crystal of the present invention was preferentially crystallized, and the Form-II crystal of the present invention was crystallized only in water-containing systems that are not used in production of pharmaceutical bulk drugs, such as water-containing acetone, water-containing ethanol, and water-containing tetrahydrofuran.

Test Example 2 Stability Test

The Form-II crystal of the compound A was put in a glass bottle, and the glass bottle was tightly sealed and stored at 90° C. The sample was taken out after 1 day, 3 days, and 7 days, and was dissolved in methanol at a concentration of 1 mg/mL. Each solution was subjected to measurement of analogs by HPLC. As for the crystals after 7 days, the crystal form was confirmed. The results are shown in Table 4.

TABLE 4

| Storage condition | Form-II Appearance | Form-II HPLC area (%) |
|---|---|---|
| Before storage | pale yellow crystal | 99.7 |
| 90° C., after 1 day | no change | 99.7 |
| 90° C., after 3 days | no change | 99.8 |
| 90° C., after 7 days | no change | 99.6 |
| Crystal form after 7 days | Form-II | |

The results above have clarified that chemical and physical stabilities are very high in each of the crystal forms.

Test Example 3 Solvent-Mediated Transformation Test

Each solvent was added to the Form-I crystal of the compound A, and the mixture was stirred at room temperature for 24 hours, and then, insolubles was filtered to prepare a saturated solution. Mixed crystals (about 10 mg) in which the Form-I crystal and the Form-II crystal were mixed at 1:1 were added to each solution, and the resultant mixture was stirred at room temperature for 5 days. Formed crystals were collected through filtration, and the crystal form thereof was confirmed. The results are shown in Table 5.

TABLE 5

| Solvent | Crystal form in saturated solution | Crystal form of seed crystal | Crystal form after 1 day | Crystal form after 5 days |
|---|---|---|---|---|
| acetonitrile | Form-I | Form-I + Form-II (1:1) | Form-I | Form-I |
| ethyl acetate | Form-I | | Form-I + Form-II | Form-I |
| acetone:water 20:80 | Form-I | | Form-I | Form-I |

As shown above, the mixed crystals of the two types of crystal forms were all transformed to the Form-I crystal of the present invention after 5 days, in acetonitrile, ethyl acetate, and the water-containing acetone at room temperature. This result has clarified that the Form-I crystal of the present invention is thermodynamically stable in each solvent.

The invention claimed is:

1. A Form-I crystal of (S)-$N^2$-[(1-(4-fluorophenyl)ethyl]-4-(1-methyl-1H-pyrazol-4-yl)-$N^6$-(pyrazin-2-yl)pyridine-2,6-diamine maleate, showing diffraction peaks in its X-ray powder diffraction spectrum at least at the following angles of diffraction 2θ: 6.9 degrees, 9.4 degrees, 12.5 degrees, 15.1 degrees, 16.4 degrees, 18.3 degrees, 19.0 degrees, 24.9 degrees, 25.4 degrees, 27.3 degrees, and 27.7 degrees, wherein X-ray powder diffraction spectrum is obtained by utilizing Cu Kα radiation (λ=1.54 Å).

2. A Form-I crystal of (S)-$N^2$-[1-(4-fluorophenyl)ethyl]-4-(1-methyl-1H-pyrazol-4-yl)-$N^6$-(pyrazin-2-yl)pyridine-2,6-diamine maleate, having an endothermic peak at 203±3° C. in differential scanning calorimetry.

3. A pharmaceutical composition containing the crystal according to claim 1 as an active ingredient and a pharmaceutically acceptable carrier.

4. A pharmaceutical composition containing the crystal according to claim 2 as an active ingredient and a pharmaceutically acceptable carrier.

5. The crystal according to claim 1, having an endothermic peak at 203±3° C. in differential scanning calorimetry.

6. A pharmaceutical composition containing the crystal according to claim 5 as an active ingredient and a pharmaceutically acceptable carrier.

* * * * *